(12) United States Patent
Glaser

(10) Patent No.: US 6,745,635 B2
(45) Date of Patent: *Jun. 8, 2004

(54) PROOF LOAD TEST GAUGE FOR SWAG BEARING

(76) Inventor: Ronald J Glaser, 824 Orchard Ave., Avalon, PA (US) 15202

( * ) Notice: Subject to any disclaimer, the term of this patent is extended or adjusted under 35 U.S.C. 154(b) by 0 days.

This patent is subject to a terminal disclaimer.

(21) Appl. No.: 10/053,146

(22) Filed: Jan. 23, 2002

(65) Prior Publication Data
US 2003/0136198 A1 Jul. 24, 2003

(51) Int. Cl.$^7$ .................................................. G01N 3/10
(52) U.S. Cl. .................................................. 73/825; 73/802
(58) Field of Search ........................... 73/825, 864.16, 73/798, 802

(56) References Cited

U.S. PATENT DOCUMENTS

| | | | | |
|---|---|---|---|---|
| 2,439,035 A | * | 4/1948 | Bidwell et al. | 73/865.9 |
| 3,201,996 A | * | 8/1965 | Silvia | 73/865.9 |
| 3,646,496 A | * | 2/1972 | Williams | 439/462 |
| 5,133,211 A | * | 7/1992 | Brown et al. | 73/118.1 |
| 5,187,987 A | * | 2/1993 | Anderson et al. | 73/852 |
| 5,490,432 A | * | 2/1996 | Allard et al. | 73/865.9 |

* cited by examiner

Primary Examiner—Edward Lefkowitz
Assistant Examiner—Takisha S Miller

(57) ABSTRACT

An improved device for proof load testing of bearings comprising of a cylinder body (8) and a piston (3) which are slidably mounted with a male and female internal coupling design, creating an cylindrical type cavity (9) within the body. The cavity is filled with hydraulic fluid. An axial bore hole (10) extends through the center of the piston and cylinder. A threaded enlongated bolt (1) is extended through the axial bore hole and a bearing assembly and into a threaded recessed receiver die (6). The bolt is tightened, forcing the device against the bearing assembly and the forcing the bearing against the recessed area of the receiver die. The pressure created by tightening the bolt is measured by a hydraulic gauge (12) attached to the cylinder body. When predetermined pressure by the tightened bolt is reached on the hydraulic gauge, a mechanical gauge attached to the receiver die is examined to verify or prove the bearing has withstood the load within manufacturer's specified tolerances.

4 Claims, 3 Drawing Sheets

PROOF LOAD TEST GAUGE FOR SWAG BEARING

CROSS-REFERENCE TO RELATED APPLICATIONS

Not Applicable.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This patent relates to a previously filed Disclosure Document filed with the United States Patent and Trademark Office in Disclosure Document Number 494,284 on May 25, 2001. In that document the inventors disclosed a device for proof load testing of a swaged lip bearing, such as used in the airline industry. The bearing is placed into its position within its housing and permanently installed by the rolling or "swaging" of its lip around the hole into which it is installed. After the swaging, the bearing must not move when placed under a predetermined load. It is required to be tested for movement under such load. The device is used to apply a predetermined load factor on a swaged bearing and detect and measure any movement on the bearing. This device is novel in that it replaces more comnlex "H" frame type hydraulic presses or a hand pump hydraulic unit. These complex testing units utilize hydraulic presses used for other applications. This use can create the potential for error in that the conversion of the PSI from one application to another application may not directly correlate. Mathematical computations must be double-checked by a competent engineer to verify the conversion of the PSI of the hydraulic press to the tested bearing. The methods not only have potential for error but are cumbersome in that the Dart housing the bearing must be removed for testing in the "W" frame and reinstalled. The portable hand held hydraulic pumps used for field testing bearings require that the press be leveraged between the bearing and a separate support or brace. This may not be possible given the difficulty of the bearing location and the lack of a suitable supporting brace for leverage.

Specifically this device is unique because it is small, easy to operate, fully calibrated for the PSI required for the bearing test, may be used in the aircraft without removal of the part being tested, and creates its own pressure without requiring leverage from another object or support brace. The leverage is created by tightening a bolt which passes through the device on one side of the bearing and has a threaded receiver die on the other side which acts as a nut which grips the bolt and creates pressure against the bearing as the bolt is tightened. The bolt passes through the center of the device and squeezes the device as it is tightened. The device is filled with hydraulic fluid. A gauge is attached to the device which measures the pressure of the hydrauilic fluid in the correct PSI for the test. The bolt is tightened until the predetermined PSI is applied to the bearing. A measuring device attached to the receiver die opposite the device detects and measures any movement in the bearing.

2. Discussion of Prior Art

Prior art in this field which uitilizes hydraulic pressure to test bearing does so using a separate and independent hydraulic pump in which a predetermined amount of pressure is applied against the wheel bearing. This was disclosed in U.S. Pat. No. 5,940,432 by Allard et al. in which a separate and independent hydraulic pump is part of a kit which combines to test wheel bearing in the field. This method of testing bearing required a manually operated hydraulic pump by an operator in which bearing were either installed or removed by applying such pressure against a bearing set between a receiver die and a driver die. In this manner a wheel bearing is either installed, removed, or tested depending upon which die set is used. The center pull press utilizes a threaded pull rod shaft coupling the press through the center of the wheel bearing between the dies. The threaded rod is used for fastening purposes and does not in of itself created the pressure to perform the operation at hand. It is the separate and independent hydraulic hand pump which exerts pressure upon the bearing as it is forced by the pump between the dies.

Also, in U.S. Pat. No. 5,187,987, by Anderson et al., it was disclosed by the inventors the use of a gas bearing for a piston and drive shaft upon which pressure was applied for the purpose of measuring creep stiffness of a specimen, for example, asphalt cement. In this invention the gas bearing on the piston is an air bearing in which compressed air is forced into a cylinder housing the piston for the purpose of lifting the piston and its drive shaft to a weight of zero gravity, thereby removing the weight of the piston from the measurement of the amount of pressure applied to the specimen by a separate and independent load. The piston has a loading shaft that extends away from the piston through the cylinder then through an aperture in the cylinder seal. The gas pressure exerts pressure on the piston and the loading shaft but has little mechanical obstruction of the escape of the pressurized gas around the wall of the driveshaft through the aperture in the cylinder seal. The loading shaft applies the load to the test specimen utilizing pressure applied from a separate and independent source. This is a very complicated testing device and its application is not relevant to wheel bearing tests.

In U.S. Pat. No. 3,201,996, by Silvia, the testing device was to measure spin-bearing instability as the wheel bearing is revolved about a fixed axis. It measures the spatial location and arbitrary point of the rotor with each rotation to determine the gyroscopic integrity of the wheel bearing assembly.

In U.S. Pat. No. 5,133,211, by Brown et al., the invention simulates wear on wheel bearing by exerting a loads from various directions while spinning the wheel bearing by use of a rotating member.

In U.S. Pat. No. 2,439,035, by Bidwell, the invention simulates wear on wheel bearings by exerting a loads from various eccentric weights on a shaft while spinning the wheel bearing by use of a rotating member.

In U.S. Pat. No. 3,643,496, by Zajic, the inventors simulate press and pull pressure by suspending the tested material between hydraulic elastic steel cushions. It is designed for testing of materials and not wheel bearings.

Accordingly, several objects and advantages of this invention are to provide a means for field testing bearings by subjecting them to predetermined amounts of pressure without removing them from their location in the aircraft, and to do it easily, quickly, accurately and reliably, and without the aid of any separate, independent, or other pressure creating devices. This device accomplishes these objects and can reduce the time, expense, and potential for error caused by using other methods or devices.

BRIEF SUMMARY OF THE INVENTION

In accordance with the present invention a proof load test gauge for various ring bearings is used for the purpose of testing for movement in a bearing within a housing when the bearing is subjected to a predetermined load factor. Hydraulic pressure does not create the force, it merely measures the force created by manually tightening a threaded bolt which passes through the device and the wheel bearing and is threaded into a receiver die. The hydraulic fluid in the device which measures the pressure is obstructed from contact with the threaded bolt and from release around the threaded bolt through the apertures at either end of the device. In this way it simplifies the field testing by requiring only the device and a hand wrench to test a wheel bearing. The device has a cylinder body having a round interior hollow cavity containing a axial centered cylindrical solid protrusion which defines an "O" shaped cylinder space or cavity. A piston is slidably mounted within the cylinder body and has an axially centered cylindrical hollow cavity creating an "O" shaped piston which fits into the "O" shaped cylinder body. The piston and cylinder body have an axially extended bore hole which passes through them. The walls of the cylinder and the cylinder protrusion have "O" rings which prevent hydraulic fluid contained within the cylinder from leakage. A bolt is placed through the axial bore hole and through the bearing being tested, positioning the device on one side of the bearing. A receiver die having a threaded hole is placed on the other side of the bearing and rests against the bearing assembly. The receiver die has a recessed surface area around the bearing permitting the bearing the be forced into this area to detect movement. A hydraulic gauge is affixed to the cylinder body which measure the amount of pressure being created against the bearing as the bolt is tightened into the receiver die. A gauge is attached to the receiver die which detects and measures movement in the bearing when the bearing is subjected to a predetermined amount of pressure as the bolt is tightened.

BRIEF DESCRIPTION OF THE SEVERAL VIEWS OF THE DRAWINGS

Drawing Figures

Figure 1:
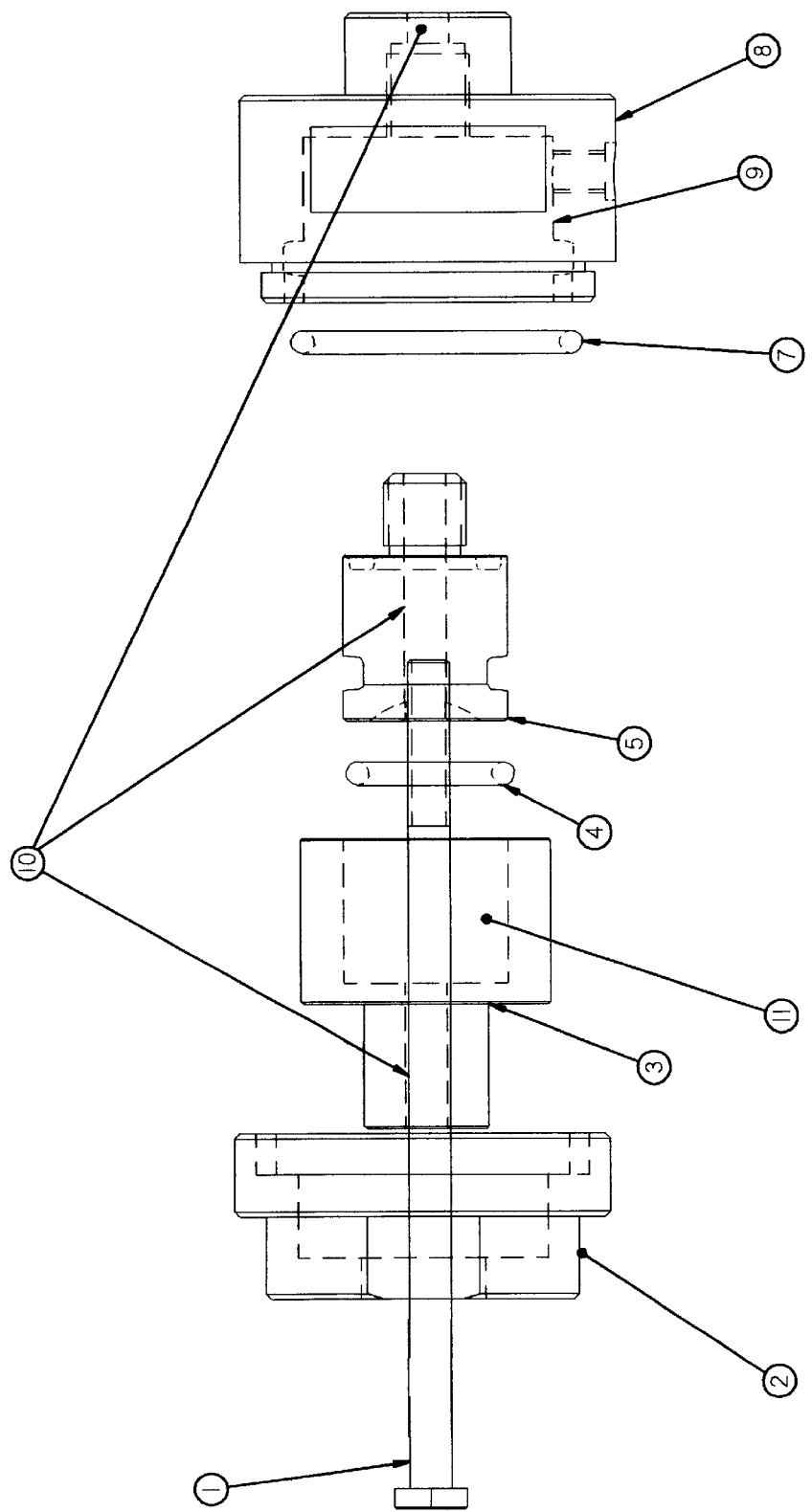
FIG. 1 shows an exploded view of the component parts of the invention.

Reference Numerals in drawings 1 bolt
2 threaded cap
3 piston
4 "O" ring
5 cylinder protrusion
6 receiver die
7 "O" ring
8 cylinder body
9 cylinder cavity
10 axial bore hole
11 piston cavity
12 gauge
13 bearing assembly/swaged bearing

DETAILED DESCRIPTION OF THE DRAWING

Description

Figure 2:
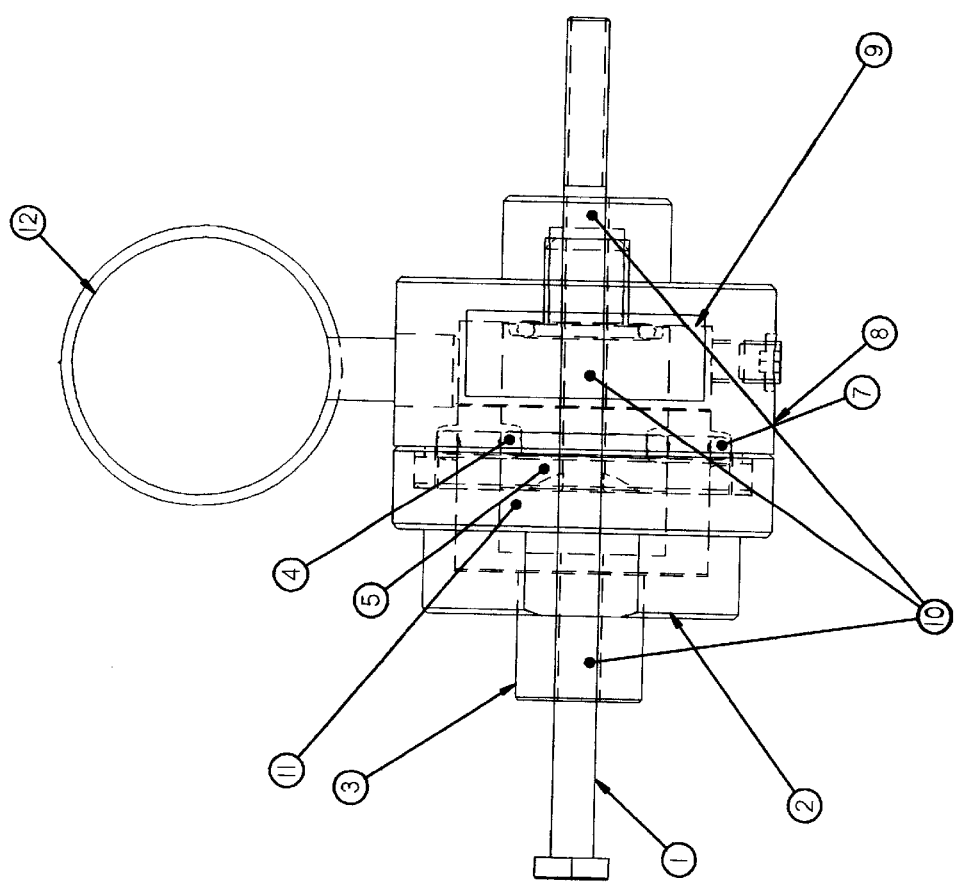
FIG. 2 shows an assembled view of the cylinder and cylinder insert.
Figure 3:
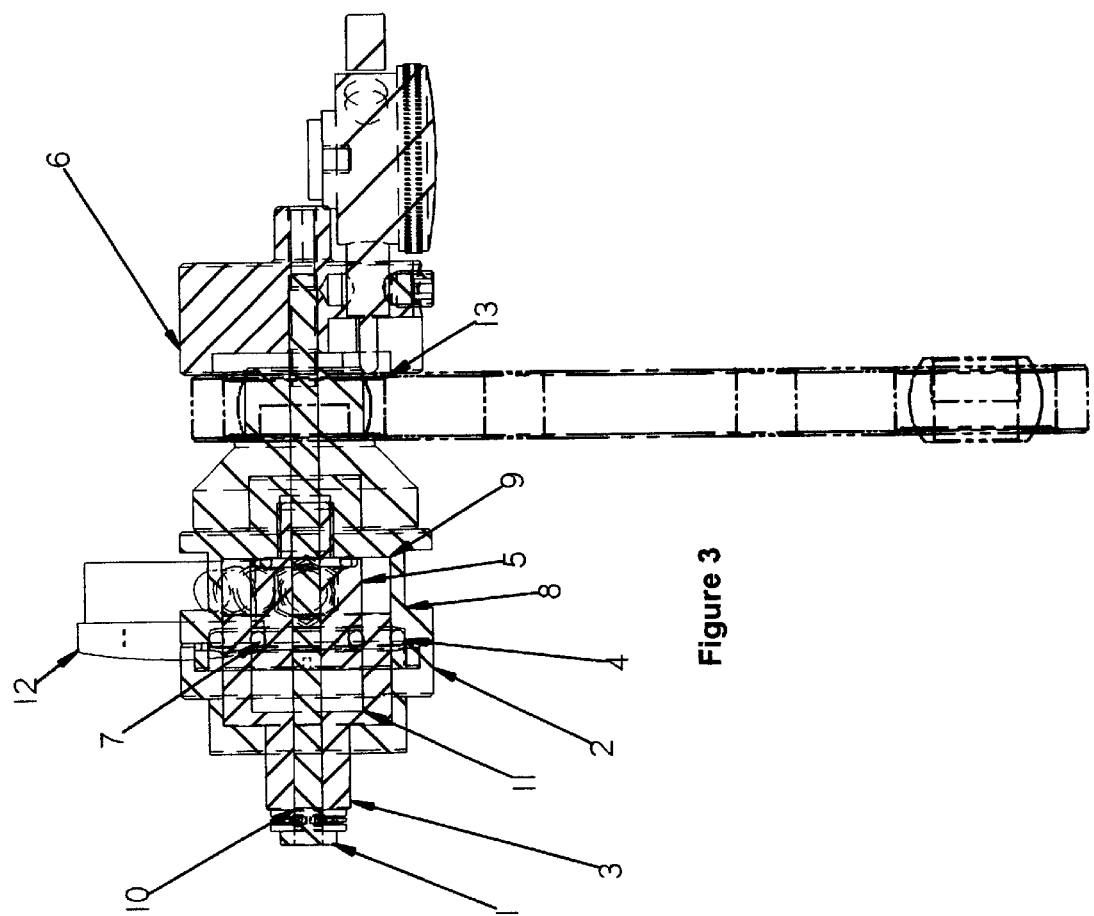
FIG. 3 shows an enlarged cross sectional view of the hydraulic chamber.

The typical embodiment of the proof load test gauge of the present invention is illustrated in FIGS. 1 through 3.

FIG. 1 shows an exploded view of the device. The device comprises of a cylinder body 8, having a round cylinder protrusion 5 which creates an "O" shaped cylinder cavity. The piston 3 has a hollow center creating an "O" shaped piston which is slidably mounted in the "O" shaped cylinder. A threaded cap 2 is placed over the piston and tightened onto the threaded exterior wall of the cylinder body. All of the described parts have an axial bore hole 10 extending through their center. A threaded bolt 1 passes through the parts and is placed through the bearing with the cylinder body resting against the bearing. The bolt is tightened into a threaded receiver die (not shown) on the other side of the bearing.

FIG. 2 shows and assembled view of the device. It shows the axial bore hole 10 which extends through the parts. It also shows the pressure gauge 12 attached to the cylinder body which measures the pressure of the hydraulic fluid created when the bolt is tightened into the receiver die.

FIG. 3 shows a cross-sectional view of the cylindrical cylinder chamber formed by the coupling of the cylinder body with the piston.

What is claimed is:

1. A proof load test device of various bearings comprising of:

(a) a cylinder body having a longitudinal axis having opposite first and second ends, one of said ends being open to a hollow round cylinder formed within the wall of the cylinder body, the other end being solid, and further having an axial extending solid cylinder protrusion extending at the center of a solid cylinder end through the cylinder, creating a cylindrical form cylinder cavity;

(b) a piston having a an axially extending hollow cavity within its body creating a cylindrical piston slidably mounted within the cylinder creating a closed chamber within the cylindrical cavity;

(c) an axial bore hole extending through the center of said piston and said cylinder;

(d) fluid within the chamber formed by coupling the piston and cylinder;

(e) a means forcing the piston into the cylinder;

(f) a means of preventing the release of fluid from the cylinder and the axial bore hole as the piston is forced into the cylinder.

2. The device as claimed in 1 wherein the means of forcing the piston into the cylinder comprises of an enlongated threaded bolt which extends through the axial bore hole on one end, and is tightened into a threaded receiver die on the other end. The die has a recessed area which permits a bearing assembly placed between the device and the receiver die to move as a swaged bearing is being pressure tested by the device.

3. The device of claim 1, wherein the means of preventing release of the fluid from the axial bore hole and cylinder comprises of "O" ring washers placed on the inner walls of the cylinder body and the outer wall of the cylinder protrusion.

4. The device of claim 1, further having a pressure gauge attached to the cylinder.

* * * * *